United States Patent [19]

Gottardi

[11] Patent Number: 4,849,215

[45] Date of Patent: Jul. 18, 1989

[54] PHARMACEUTICAL IODOPHOR PREPARATIONS WITH CONTROLLED IODINE:IODIDE RATIO AND METHOD OF PRODUCING THE SAME

[75] Inventor: Waldemar Gottardi, Insbruck, Austria

[73] Assignee: Euroceltique, S.A., Luxembourg

[21] Appl. No.: 1,846

[22] Filed: Jan. 9, 1987

Related U.S. Application Data

[63] Continuation of Ser. No. 744,154, Jun. 13, 1986, abandoned, which is a continuation of Ser. No. 584,427, Mar. 2, 1984, abandoned.

[30] Foreign Application Priority Data

Mar. 2, 1983 [DE] Fed. Rep. of Germany ....... 3307219
Apr. 15, 1983 [DE] Fed. Rep. of Germany ....... 3313655

[51] Int. Cl.$^4$ ................... A61K 31/79; A61K 33/18; A01N 59/12
[52] U.S. Cl. ................... 424/80; 424/667; 424/669; 424/672
[58] Field of Search ................ 424/80, 150

[56] References Cited

U.S. PATENT DOCUMENTS

| | | | |
|---|---|---|---|
| 2,706,701 | 4/1955 | Beller et al. | 424/150 |
| 3,288,708 | 11/1966 | Cordle et al. | 424/150 |
| 3,355,386 | 11/1967 | Contor et al. | 424/150 |
| 4,148,884 | 4/1979 | Thorogood | 424/150 |

OTHER PUBLICATIONS

CRC Handbook of Chemistry and Physics, 57th Edition (1977) p. D-142.

*Primary Examiner*—Douglas W. Robinson
*Assistant Examiner*—Roger E. Gobrogge
*Attorney, Agent, or Firm*—Steinberg & Raskin

[57] ABSTRACT

The microbicidal effectiveness of pharmaceutical iodophor preparations comprising an organic substance which reacts with iodine to form a complex thereof, such as polyvinylpyrrolidone, iodine bound thereto in complex form, free iodine, and iodide ions, is assured by controlling the ratio of total iodine (complex bound iodine and free iodine) to iodide ions at between 2:1 and 10:1, this ratio being adjusted without chemical oxidizing agents such as iodate ions by anodic oxidation of a solution of the iodophor preparation and iodide ions. The resulting preparation can be free of chemical oxidizing ions such as iodate ions.

2 Claims, No Drawings

PHARMACEUTICAL IODOPHOR PREPARATIONS WITH CONTROLLED IODINE:IODIDE RATIO AND METHOD OF PRODUCING THE SAME

This is a continuation of application Ser. No. 744,154, filed June 13, 1986, now abandoned, which is in turn a continuation of Ser. No. 584,427, filed Mar. 2, 1984, now abandoned.

BACKGROUND OF THE INVENTION

Iodophor preparations are known and are commercially available. These preparations which are complexes of iodine with an organic substance such as a polymer, surface active agent, alcohol, polyol or water soluble solvent possess considerable advantages over iodine, iodine tinctures, etc. The most important iodophor preparation is that of polyvinylpyrrolidone-iodine (PVP iodine), which is a commercially available preparation found in a variety of forms. This preparation has recognized good microbicidal properties.

However, these iodophor preparations, even including PVP iodine, also possess disadvantages which are important for the use, particularly with regard to storage stability, reliable effectiveness over an extended period and reproducibility, i.e. manufactured to a consistently good effective quality.

It has been found that predictable good microbicidal effectiveness of iodophor preparations can be assured by providing compositions of iodophor preparations comprising the iodophor-forming organic substance such as polyvinylpyrrolidone, complex bound iodine, that is iodine bound thereto, free iodine and iodide ions with a ratio of total iodine (complex bound iodine plus free iodine) to iodide of between 2:1 to 10:1, preferably 2:1 to 6:1, most preferably 2.1:1 to 3.6:1. The adjustment of this iodine to iodide ratio was effected by chemical oxidation, particularly by the addition of a source of iodate ions.

SUMMARY OF THE INVENTION

In accordance with the present invention the iodine to iodide ratio in pharmaceutical iodophor preparations of the type discussed above is suggested within the limits so as to assure the presence of free iodine without chemical oxidation by the use of anodic oxidation.

It is a primary object of the present invention to provide for pharmaceutical iodophor preparations containing free iodine and a total iodine to iodide ratio between 2:1 and 10:1 without the use of chemical oxidizing agents.

It is a further object of the present invention to provide pharmaceutical iodophor preparations with predictable microbicidal activity, containing free iodine and total iodine to iodide ratios with specific limits by means of anodic oxidation.

Other objects and advantages of the present invention will be apparent from a further reading of the specification and of the appended claims.

With the above and other objects in view, the present invention mainly comprises a method of producing pharmaceutical iodophor preparations comprising an organic substance which complexes with iodine, complex-bound iodine bound to said complex substance, free iodine and iodide ions, comprising the steps of subjecting a solution of the organic substance complex with iodine, free iodine and a source of iodide ions to anodic oxidation until the ratio of total iodine consisting of complex bound iodine and free iodine, to iodide is between 2:1 and 10:1, whereby the resulting solution contains free iodine and exhibits a high degree of antimicrobial effectiveness.

The invention is applicable to iodophor-forming organic compounds of all types, including polymers, surface active agents, alcohols, polyols and water soluble substances, these art typified complexing agents being disclosed in U.S. Pat. Nos. 1,970,578; 2,213,477; 2,674,619; 2,931,777; 2,759,869; 3,028,299; 3,028,300; 4,113,857 and many others.

It is preferred in accordance with the present invention that the anodic oxidation be continued until the total iodine to iodide ratio is preferably between 2:1 and 6:1, most preferably between 2.1:1 and 3.6:1.

It is further preferred that the iodophor preparation produced by this method contain between 2 and 20 ppm of free iodine, preferably between 2–8 ppm of free iodine.

The pH of the resulting iodophor preparation can be adjusted to between 4–6.5, preferably 5–6, for compositions for use in connection with animal tissue such as human tissue, while lower pH values can be used and higher values of free iodine can be used for compositions for the treatment of inanimate objects.

The method of the invention can be applied to freshly prepared iodophor preparations or to older, stored preparations.

DESCRIPTION OF PREFERRED EMBODIMENTS

The following examples are given to illustrate the present invention. The scope of the invention is not, however, meant to be limited to the specific details of the examples.

EXAMPLE 1

Two graphite, stainless steel or platinum electrodes are placed into 100 ml of a one year old 10% polyvinylpyrrolidoneiodine (polyvinylpyrrolidone K 30, also known as Povidone K 30) solution in water containing 1.0 g of titratable iodine and 0.5 g iodide (iodine to iodide ratio=2:1). The electrodes are connected with a direct current source. At a potential difference of 6 Volt, the iodide ions are anodically oxidized at room temperature. The iodine formed reacts with the PVP while stirring. The anodic oxidation process is continued while stirring until the titratable iodine content is 1.2 g. During this process the iodide content is reduced to 0.3 g. Thus, the iodine to iodide ratio is 4:1. The solution contains free iodine in an amount of about 2 ppm. The solution shows excellent antimicrobial effectiveness.

EXAMPLE 2

Two graphite, stainless steel or platinum electrodes are placed into 100 ml of a one year old 10% povidone iodine solution in water containing 1.0 g titratable iodine and 0.5 g iodide (iodine to iodide ratio=2:1). The electrodes are connected to a direct current source. At a potential difference of 6 Volt, the iodide ions are anodically oxidized at room temperature. The iodine formed separates at the anode surface without stirring. The oxidation process is continued until the iodine to iodide ratio of 4.0:1 is obtained, with a titratable iodine content of 1% and an iodide content of 0.25%. The separated iodine is removed together with the electrode. The solution has excellent antimicrobial effectiveness.

EXAMPLE 3

10 g of PVP iodine containing 10% iodine are dissolved in 100 ml water at room temperature while stirring. Potassium iodide is added and the solution is subjected to a direct current at a potential difference of 6 Volt using two graphite electrodes. The iodide ions are anodically oxidized at room temperature and the anodic oxidation is continued to provide an iodine to iodide ratio of 3.6:1 and a free iodine content of 5 ppm. The pH of the solution is raised to 5.0-5.5 by the addition of citric acid and soda lye. The solution has excellent antimicrobial effectiveness.

While the invention has been described with respect to particular iodophor preparations and methods of producing the same, it is apparent that variations and modifications of the invention can be made.

What is claimed is:

1. Method of producing a pharmaceutical iodophor preparation, which comprises subjecting a solution of polyvinylpyrrolidone, iodine and iodide ions to anodic oxidation to convert iodide ions to iodine and form an oxidized solution containing polyvinylpyrrolidone complexed with iodine, free iodine and iodide ions, said anodic oxidation being continued until said oxidized solution has a ratio of total titratable iodine, consisting of complex-bound iodine and free iodine, to iodide of between 2.1:1 and 36:1 and said solution contains free iodine in an amount of between 2 and 20 ppm, and adjusting the pH of said oxidized solution to between 5 and 6.

2. Method according to claim 1 wherein said anodic oxidation is continued until the concentration of free iodine is between 2 and 8 ppm.

* * * * *